United States Patent [19]  
Sato et al.

[11] Patent Number: 4,895,805  
[45] Date of Patent: Jan. 23, 1990

[54] CELL MANIPULATING APPARATUS

[75] Inventors: Kazuo Sato, Tokyo; Shinji Tanaka, Akishima; Yoshio Kawamura, Kokubunji; Hiroyuki Kohida, Fuchu; Yoshihisa Hosoe; Masatoshi Sakurano, both of Shimizu, all of Japan

[73] Assignee: Hitachi, Ltd., Tokyo, Japan

[21] Appl. No.: 235,485

[22] Filed: Aug. 24, 1988

[30] Foreign Application Priority Data

Aug. 31, 1987 [JP] Japan .................................. 62-215288

[51] Int. Cl.$^4$ .............................................. C12M 3/02
[52] U.S. Cl. .................................... 435/286; 435/300; 210/416.1
[58] Field of Search ............... 435/286, 291, 300, 814; 436/807, 808, 809; 210/406, 411, 416.1

[56] References Cited

U.S. PATENT DOCUMENTS 4,252,897  2/1981  Axford et al. ...................... 435/291
4,272,510  6/1981  Smith et al. ......................... 436/807
4,729,949  3/1988  Weinreb et al. .................... 435/291

FOREIGN PATENT DOCUMENTS 0154686  9/1985  European Pat. Off. ............ 436/809
62-32874  12/1987  Japan .................................. 435/291

Primary Examiner—James C. Yeung  
Assistant Examiner—Alan Cariaso  
Attorney, Agent, or Firm—Antonelli, Terry & Wands

[57] ABSTRACT

Disclosed is a cell manipulating apparatus for conveying cells to a plurality of chambers provided in a chamber plate. The apparatus comprises a taking-up device adapted to take up cells to the respective taking up portions of a carrier plate placed in positions corresponding to those of said chambers in the chamber plate and a moving device adapted to move, relatively with respect to the chamber plate, the taking-up device to a position above the chamber plate. The taking-up portions may be effectively composed of pressure-controlled cavities or SiO$_2$ films provided in the carrier plate.

10 Claims, 6 Drawing Sheets

CELL MANIPULATING APPARATUS

BACKGROUND OF THE INVENTION

This invention relates to an apparatus for conveying cells to a plurality of chambers provided in a chamber plate.

Recently, a type of cell fusion system has become established in which cells of different sorts are conveyed one by one to each of the chambers of a chamber plate before cell fusion of these cells is undertaken.

In conventional cell manipulating apparatuses (see, for example, Japanese patent laid-open No. 62-32874), cells are conveyed through a channel having openings. Each opening is successively positioned above each chamber so that cells can be individually injected into it. A similar apparatus is disclosed in U.S. patent application Ser. No. 122269 "Chamber plate for use in cell fusion and a process for production thereof" filed on Nov. 18, 1987.

Since in cell manipulating apparatuses having the above-described construction it is necessary to position the opening successively above each of the chambers, when there are a great number of chambers in the chamber plate, it takes a lot of time to furnish all the chambers with cells. This is particularly disadvantageous in the case of protoplasts whose cell walls have been removed by means of an enzyme since they lose their activity in a short time. When protoplasts are conveyed to a large number of chambers, those protoplasts which are conveyed during the earlier stage of the conveying operation will lose their activity before the conveying operation has been completed. Consequently, the number of protoplasts that can undergo cell fusion at a time has been limited.

SUMMARY OF THE INVENTION

This invention is intended to overcome the above-mentioned problem, and it is an object of this invention to provide a cell manipulating apparatus capable of conveying cells to the chambers provided in a chamber plate within a reduced period of time.

In accordance with this invention, the above object can be attained by a cell manipulating apparatus for conveying cells to a plurality of chambers provided in a chamber plate, comprising: a taking-up device adapted to take up said cells to taking-up portions which are placed such as to face the respective chambers of said chamber plate; and a moving device adapted to relatively move said taking-up device to a position above said chamber plate.

In this cell manipulating device, the taking-up device is relatively moved, holding taken-up cells in its taking-up portions, to a position over the chamber plate. After positionally matching the taking-up portions with the chambers, the cells are released from the taking-up portions, thus transferring all of the cells to the respective chambers of the chamber plate at one time.

The taking up device may be composed of taking-up portions comprising penetrating holes and cavities connected thereto formed in a carrier plate, the pressure within said penetrating holes being lowered so as to take up cells on the carrier plate.

It is also possible to form the carrier plate from single crystal silicon and to form thereon films of $SiO_2$ which act as taking-up portions, cells being adsorbed due to their hydrophilic property.

DETAILED DESCRIPTION OF THE PREFERRED EMBODIMENTS

Figure 1:
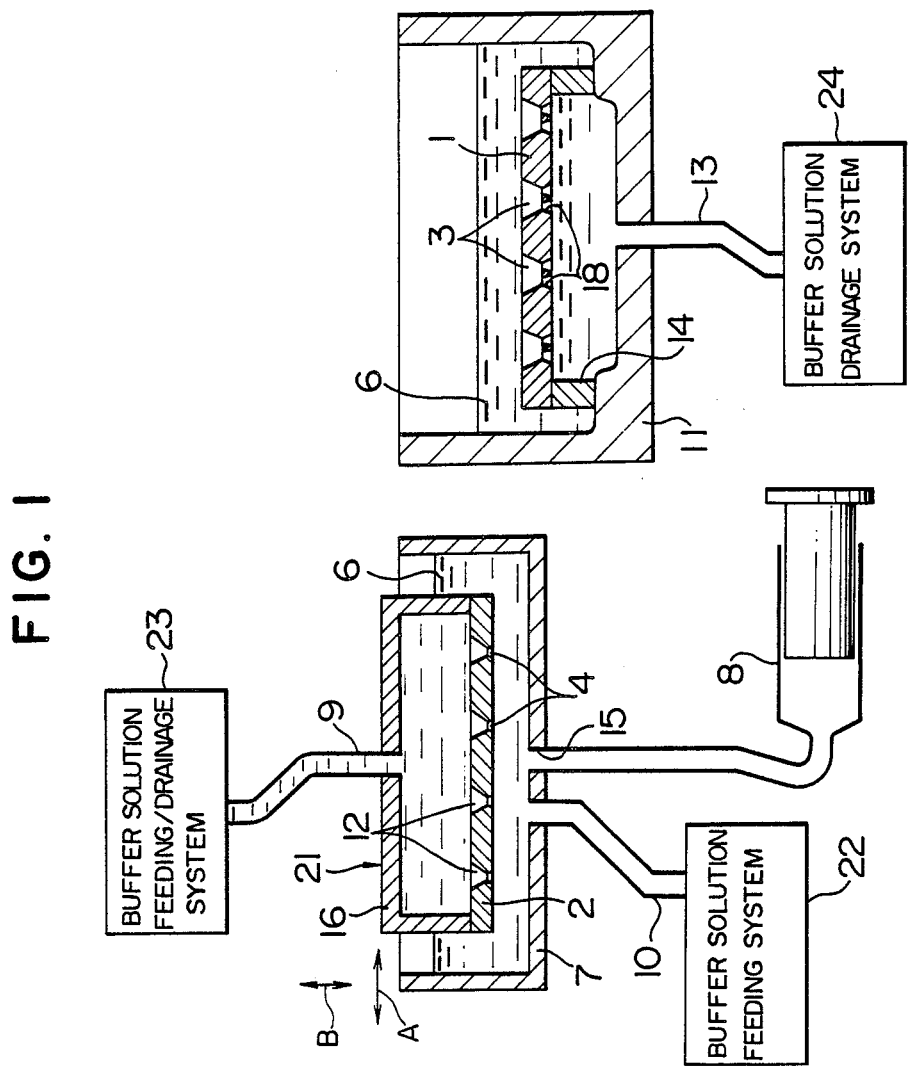
FIG. 1 is a schematic sectional view of an embodiment of the cell manipulation apparatus in accordance with this invention.
Figure 2:
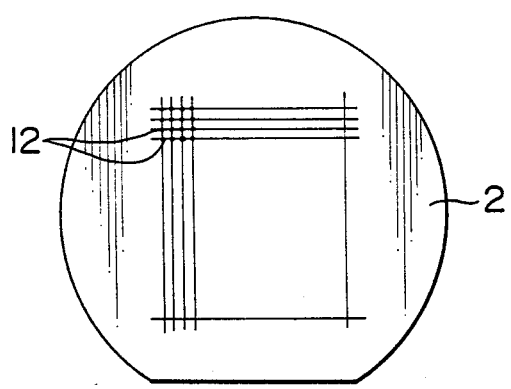
FIG. 2 is a plan view of the carrier plate of the cell manipulating apparatus shown in FIG. 1.
Figure 3:
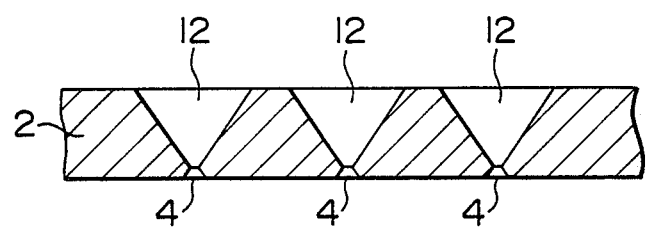
FIG. 3 is an enlarged sectional view of the carrier plate.
Figure 4:
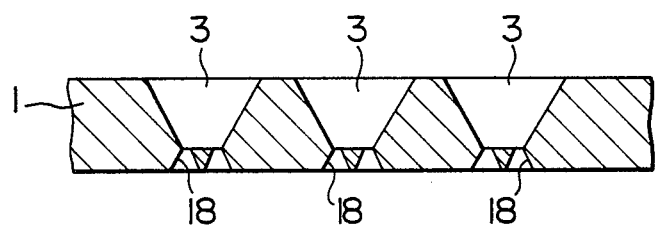
FIG. 4 is an enlarged sectional view of the chamber plate of the cell manipulating apparatus shown in FIG. 1.

Preferred embodiments of this invention will now be explained referring to the attached drawings. As shown in FIG. 1, one end of a drain tube 13 is connected to the bottom of a container 11 and the other end thereof is connected to a buffer solution drainage system 24. A chamber plate 1 is fixed to a support member 14 arranged in the container 11. This chamber plate 1 is made from single crystal of silicon and has a thickness of 0.4 mm and a diameter of 75 mm. The chamber plate 1 has therein a plurality of chambers 3 arranged in a 45×45 matrix-like manner with a pitch of 0.8 mm. As shown in FIG. 4, slits 18 communicating with the chambers 3 are provided at the bottom of the chambers 3. One end of a feed pipe 10 is connected with the bottom section of a container 7 and the other end thereof is connected to a buffer solution feeding system 22. A connecting hole 15 for connecting an injection apparatus 8 is also provided at the bottom of the vessel 7. As shown in FIGS. 2 and 3 in detail, the carrier plate 2 formed from single crystalline silicon wafer has a thickness of 0.4 mm and a diameter of 75 mm. Cavities 4 are provided at the bottom of the carrier plate 2. These cavities 4 are arranged to correspond in position and number (45×45) to those of the chambers 3. Provided in the carrier plate 2 are communicating holes 12 which communicate with the cavities 4. The minimum diameter of the communication holes 12 is ca. 10 μm. To the carrier plate 2 is attached a plate holder 16 to which one end of a flexible hose 9 is connected. The other end of the flexible hose 9 is connected to a buffer solution feed/drainage system 23. A taking-up device 21 which is composed of the carrier plate 2, the plate holder 16 etc. is moved by a moving device (not shown) in the vertical and the horizontal directions B, A. Provided inside the containers 7 and 11 is a buffer solution 6 such as sucrose solution.

Figure 5A:
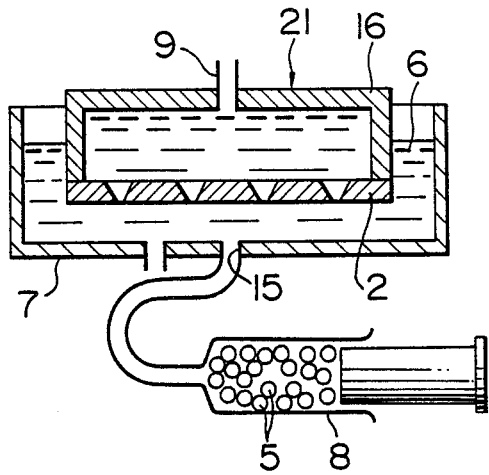
FIGS. 5A to 5F are explanatory views illustrating the operation of the cell manipulating apparatus of FIG. 1.
Figure 5B:
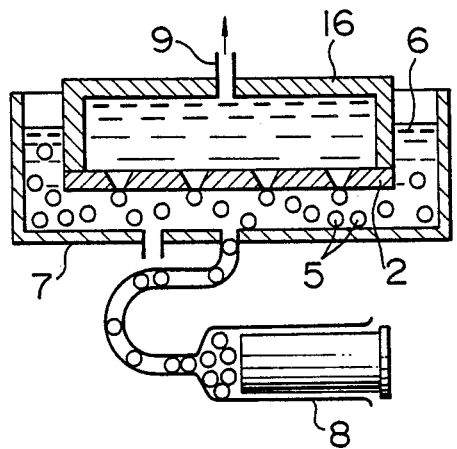
Figure 5C:
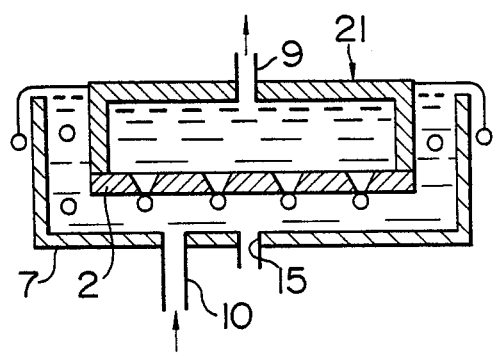
Figure 5D:
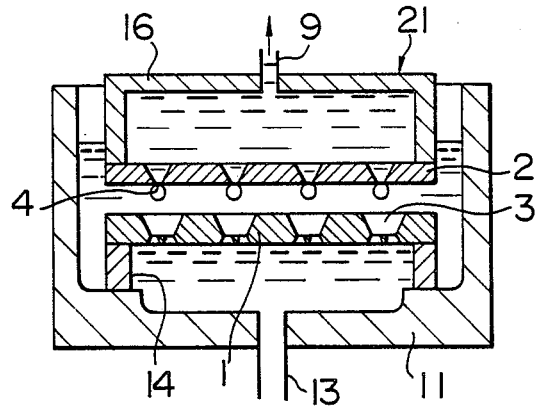
Figure 5E:
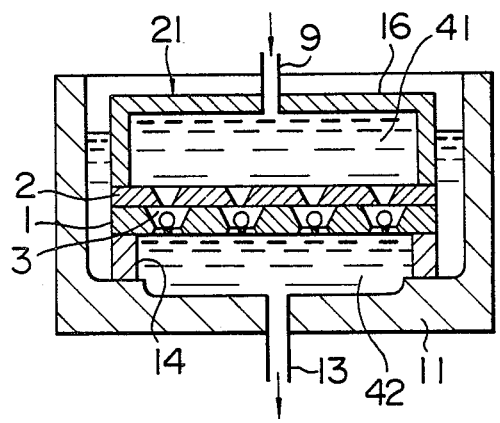
Figure 5F:
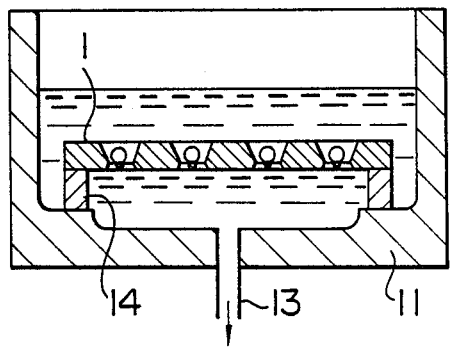

The operation of this cell manipulating apparatus thus constructed is explained hereinafter. Firstly, the buffer solution 6 containing, in suspension, plant cells 5 individually separated by the enzyme is sealed into the injection apparatus 8, as shown in FIG. 5A. Then, as shown in FIG. 5B, the injection apparatus 8 is driven so as to inject the cells 5 into the container 7. At the same time, the buffer solution 6 inside the plate holder 16 is drawn out, so that negative pressure is generated within the plate holder 16. As a result, the cells 5 are taken up to the cavities 4. The withdrawal of the buffer solution 6 in the plate holder 16 by the buffer solution feed/drainage system is continued, and at the same time, the buffer solution feeding system is controlled to feed the container 7 with buffer solution 6 through the feeding pipe 10, as shown in FIG. 5C. The buffer solution 6 then flows over the container 7, thereby driving those cells 5, which are not taken up to the cavities 4, out of the container 7. Subsequently, the moving device (not shown) moves the taking-up device 21 into the container 11, as shown in FIG. 5D, while keeping to such or applying the negative pressure to the buffer solution 6 in the plate holder 16. The taking-up device 21 is positioned such that the chambers 3 are vertically aligned or register with the cavities 4 and that the carrier plate 2 is brought into close contact with the chamber plate 1, as shown in FIG. 5E. In this condition, the buffer solution feeding/drainage system supplies the region 41 in the plate holder 16 with the buffer solution 6 to generate positive pressure at the region 41 in the plate holder 16. At the same time, the buffer solution drainage system sucks or draws out the buffer solution 6 from the region 42 in the support member 14 through the drainage pipe 13, so that negative pressure is generated at the region 42 in the support member 14. As a result, the cells 5 are released from the cavities 4 and received in the corresponding chambers 3. Subsequently, the moving device moves the taking-up device 7 from the container 11 into the container 7, while the buffer solution at the region 42 in the support member 14 is kept under a reduced pressure. In this condition, the chamber plate 1 can be taken out of the vessel 11, as shown in FIG. 5F.

Thus, in this cell manipulating apparatus, the taking-up device 21 is moved to a position above the chamber plate 1 while the cells 5 are being taken up to the cavities 4 by the liquid pressure such that the chambers 3 are aligned or positionally matched with the cavities 4, and then the cells 5 are released from the cavities 4 by the liquid pressure to causes the cells 5 to be charged into the chambers 3. Consequently, a great number of cells 5 can be conveyed or transferred to the chambers 3 at one time, so that the cells 5 can be conveyed to the chambers 3 in a very short time.

Figure 6:
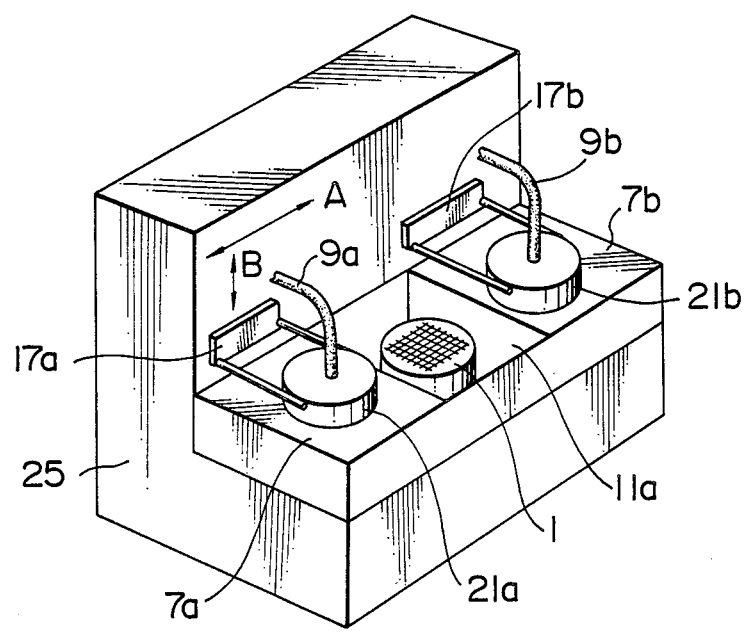
FIG. 6 is a schematic perspective view of another embodiment of the cell manipulating apparatus in accordance with this invention.

FIG. 6 is a schematic perspective view of another embodiment of the cell manipulating apparatus in accordance with this invention. This apparatus has a construction adapted to allow different sorts or species of cells to be placed in pairs into the chambers and sealed therein for the purpose of conducting cell fusion. As shown in FIG. 6, the chamber plate 1 for receiving a large number of pairs of differnt species of cells is fixed in the tank 11a in such a manner as to be submerged in the buffer solution. In individual containers 7a, 7b which are partitioned off from the tank 11a are provided with taking-up devices 21a and 21b adapted to take up differnt species of cells, respectively. Each of these taking-up devices 21a and 21b serves to convey cells of a single species to the chamber plate 1 in accordance with the procedure of FIGS. 5A to 5F. Flexible hoses 9a, 9b are connected to a buffer solution feeding/drainage system incorporated in the apparatus body 25. The containers 7a, 7b correspond to the container 7 shown in FIG. 1, the bottom of each container being connected to an injection apparatus and a buffer solution feeding system. Both of the injection apparatuses and the buffer solution feeding systems are incorporated in the apparatus body 25. A moving device 17a supporting the taking-up device 21a serves to raise and lower the taking-up device 21a in the direction of the arrow B at the position of the continer 7a and to move the taking-up device 21a in the direction of the arrow A to bring it beyond the border between the container 7a and the tank 11a to a position just above the chamber plate 1. Further, in order to bring the taking-up device 21a close to the chamber plate 1, the moving device 17a serves to move the taking-up device 21a vertically (in the direction B) also at the position cf the tank 11a. On the other hand, the moving device 17b supporting the taking-up device 21b serves, similarly, to raise and lower the taking-up device 21b at the positions of the container 7 as well as the tank 11a and to move the taking-up device 21b horizontally between the container 7b and the tank 11a.

In this cell manipulating apparatus, the moving device 17a brings the taking-up device 21a on which the first sort or species of cells are taken up to a position above the chamber plate 1. The chambers 3 and the cavities of the adsorption device 21a are aligned with each other, and the first species of cells are released from the cavities, the first species of cells being received in the respective chambers 3. Then, the moving device 17b brings the taking-up device 21b on which the second sort or species of cells are taken up to a position above the chamber plate 1. The chambers 3 and the cavities of the taking-up device 21b are then aligned with each other, and the second species of cells are released from the respective cavities, the second species of cells being received in the chambers 3 to accomodate the cell pairs in each of the chambers 3. When the chamber plate 1 in this condition is dipped in polyethylene glycol or an electrical pulse is applied, cell fusion is effected in each chamber 3.

When this cell manipulating apparatus is used for carrying out cell fusion of different sorts or species of protoplasts, a large number of protoplasts can be conveyed to the chambers in a short time, so that even when a great number of protoplasts are to be conveyed to the chambers, deterioration in the activity of protoplasts during conveyance can be avoided, the number of protoplasts which can undergo cell fusion at one time thus being remarkably increased.

Figure 7A:
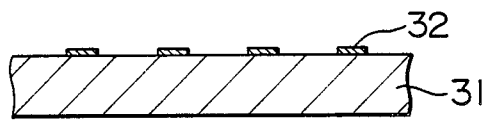
FIGS. 7A to 7D are explanatory views illustrating the operation of still another embodiment of the cell manipulating apparatus in accordance with this invention.
Figure 7B:
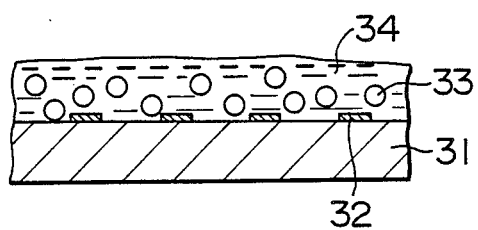
Figure 7C:
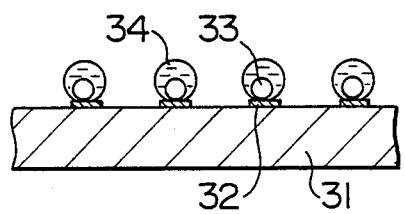
Figure 7D:
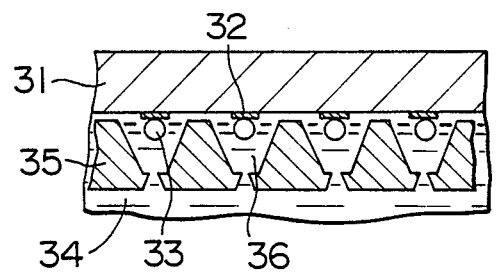

While in the embodiments above the taking-up devices 21, 21a, 21b which is adapted to take up the cells 5 to the cavities 4 by liquid pressure is used as the taking-up device, it is also possible to use a taking-up device which has taking-up or adsorbate portion composed of organic and inorganic films, where the cells can be chemically adsorbed due to their hydrophilic or other adsorbing properties. FIGS. 7A to 7D show still another embodiment of this invention. As shown in FIG. 7A, adsorbate sections composed of $SiO_2$ films 32 are provided on the surface of the carrier plate 31 made of single crystalline silicon. By feeding buffer solution 34 containing cells 33 to the surface of the carrier plate 31 as shown in FIG. 7B, the cells 33 can be adsorbed on the $SiO_2$ films 32 on account of their hydrophilic properties, as shown in FIG. 7C. The carrier plate 31 on which the cells are thus adsorbed is conveyed to a position above the chamber plate 35. The chamber plate 35 and the carrier plate 31 are then positionally matched or registerd with each other as shown in FIG. 7D. Then, by feeding the buffer solution 34 in such a manner that the carrier plate may be submerged in the buffer solution 34, the cells 32 are released from the $SiO_2$ films, so that the cells 32 can be received in the chambers 36 of the chamber plate 35.

In still another embodiment, adsorbate portions composed of polylysine films may be provided on the surface of the carrier plate instead of the above SiO$_2$ films. Cells are adsorbed on the polylysine films due to their adherent or adsorbing property. In this case, the cells can be released from the polylysine films by supplying a suitable chemical liquid. The operation is the same as that shown in FIGS. 7A to 7D.

While in the embodiments above the chambers 3 have a different configuration from that of the cavities 4, both may have the same configuration. In this case, fusion of cells pairs may be conducted under the condition where the chamber plate 1 and the carrier plate 2 are in close contact with each other. Furthermore, while in the above embodiments the number of cavities 4 is the same as that of the chambers 3, they may be different from each other. The number of cavities 4 may be less than that of the chambers 3, for example, half the number. In that case, the conveying operation may be repeated a plurality of times to convey cells 5 to all the chambers 3. Further, while in the embodiments above the cells 5 are plant cells, it should naturally be understood that this invention can be applied to animal cells. Moreover, it can also be applied to both nucleated cells and anucleate cells. Further, while in the embodiments above the taking-up device 21, 21a, 21b, etc. is moved by a moving or conveying device, it is also possible to move the chamber plate 1 by a moving or conveying device. In other words, it is required only to move the adsorption device 21, 21a, 21b, etc. relatively with respect to the chamber plate 1. Furthermore, while in the above embodiment a plurality of containers 7a, 7b, 11a are provided, it is also possible to partition a single container by means of detachable partition plates, the taking-up device 21, 21a, 21b etc. and the chamber plate 1, 35 being formed in the sections thus defined. Further, it may also be possible to cultivate syncytia in the chambers 3, while keeping the chamber plate 1 and the carrier plate 2 in close contact with each other. The chamber plate 1 and the carrier plate 2 are formed from single crystal silicon wafers. Pyramidal shaped chambers 3 and cavities 4 are precisely etched on (100) oriented wafers using potassium hydroxide (KOH) water solutions as an etchant. Anisotropic etching of the system is suitable for achieving these microstructures.

As described above, in the cell manipulating apparatus in accordance with this invention, a moving device relatively moves the taking-up device relatively with respect to the chamber plate, while keeping the cells taken up to on the taking-up portion of the taking-up device. The chambers and the taking-up portions are aligned or positionally matched with each other, and then by releasing the cells from the taking-up portions, the cells can be conveyed or transferred to the chambers of the chamber plate. It will be appreciated from this that conveyance of a great number of cells can be effected in a very short time, which is a remarkable advantage of the present invention.

What is claimed is:

1. A cell manipulating apparatus for conveying cells to a plurality of chambers provided in a chamber plate, comprising:

a taking-up device including a carrier plate having taking-up portions placed in positions corresponding to those of said chambers in said chamber plate, each of said taking-up portions being adapted to provide means for taking up a single cell and a moving device adapted to move, relative with respect to the chamber plate, said taking-up device to a position above said chamber plate to set said taking-up portions in close proximity with respect to said chambers to allow transfer of a plurality of said single cells from said taking-up device to said chamber plate at one time.

2. A cell manipulating apparatus as claimed in claim 1, wherein a plurality of said taking-up devices are provided.

3. A cell manipulating apparatus for conveying cells to a plurality of chambers provided in the chamber plate, comprising: a taking-up device adapted to take up cells to taking-up portions in a carrier plate placed in positions corresponding to those of said chambers in said chamber plate and a moving device adapted to move, relative with respect to the chamber plate, said taking-up device to a position above said chamber plate; both or either of said chamber plate and said carrier plate are or is formed from single crystal silicon.

4. A cell manipulating apparatus for conveying cells to a plurality of chambers provided in a chamber plate, comprising:

a taking-up device having a carrier plate including cavities and penetrating holes provided in positions corresponding to those of the chambers of said chamber plate and a pressure control means for controlling liquid pressure within said penetrating holes, said taking-up device having means adapted to take up and to release a single cell to and from each of said cavities, respectively;

a container in which said carrier plate is to be placed and into which buffer solution and the cells are introduced;

a cell feeding means for feeding the cells into said container; and a moving device adapted to move, relatively with respect to said chamber plate, said taking-up device which has taken up the single cells to a position above said chamber plate to allow transfer of a plurality of said single cells from said taking-up device to said chamber plate at one time by a change in liquid pressure within said penetrating holes.

5. A cell manipulating apparatus for conveying cells to a plurality of chambers provided in a chamber plate, comprising: a taking-up device having a carrier plate including cavities and penetrating holes provided in positions corresponding to those of the chambers of said chamber plate and a pressure control means for controlling the pressure within said penetrating holes, said taking-up device being adapted to take up the cells to said cavities; a container in which said carrier plate is to be placed and into which buffer solution and the cells are introduced; a cell feeding means for feeding the cells into said chamber and a moving device adapted to move, relatively with respect to said chamber plate, said taking-up device which has taken up the cells to a position above said chamber plate; said pressure control means being composed of a plate holder conveying the upper surface of said carrier plate and a means for lowering the pressure at a region in said plate holder.

6. A cell manipulating apparatus as claimed in claim 4, wherein said cell feeding means comprises an injection apparatus.

7. A cell manipulating apparatus for conveying cells to a plurality of chambers provided in a chamber plate, comprising: a taking-up device having a carrier plate including cavities and penetrating holes provided in positions corresponding to those of the chambers of said chamber plate and a pressure control means for controlling the pressure within said penetrating holes, said taking-up device being adapted to take up the cells to said cavities; a container in which said carrier plate is to be placed and into which buffer solution and the cells are introduced; a cell feeding means for feeding the cells into said chamber and a moving device adapted to move, relatively with respect to said chamber plate, said taking-up device which has taken up the cells to a position above said chamber plate; said carrier plate being formed from single crystal silicon wafer.

8. A cell manipulating apparatus for conveying cells to a plurality of chambers provided in a chamber plate, comprising: a taking-up device having a carrier plate including cavities and penetrating holes provided in positions corresponding to those of the chambers of said chamber plate and a pressure control means for controlling the pressure within said penetrating holes, said taking-up device being adapted to take up the cells to said cavities; a container in which said carrier plate is to be placed and into which buffer solution and the cells are introduced; a cell feeding means for feeding the cells into said chamber and a moving device adapted to move, relatively with respect to said chamber plate, said taking-up device which has taken up the cells to a position above said chamber plate; said chamber plate being formed from single crystal silicon wafer.

9. A cell manipulating apparatus for conveying cells to a plurality of chambers provided in a chamber plate, comprising: a taking-up device composed of a carrier plate formed from single crystal silicon and taking-up portions of $SiO_2$ films arranged on said carrier plate such as to be in positions corresponding to those of the chambers of said chamber plate, said taking-up device being adapted to take up said cells on said taking-up portions, and a moving device adapted to move, relatively with respect to said chamber plate, said taking-up device to a position above said chamber plate.

10. A cell manipulating apparatus as claimed in claim 9, wherein said chamber plate is formed from single crystal silicon wafer.

* * * * *